United States Patent
Mendelsohn (12) 
(10) Patent No.: US 6,867,008 B1
(45) Date of Patent: Mar. 15, 2005

(54) METHOD FOR ASSAYING COMPOUNDS AFFECTING CELL DIVISION USING ESTROGEN RECEPTOR BETA (ERβ) AND MITOSIS ARREST DEFICIENT 2 (MAD2)

(75) Inventor: Michael E. Mendelsohn, Wellesley, MA (US)

(73) Assignee: New England Medical Center Hospitals, Inc., Boston, MA (US)

(*) Notice: Subject to any disclaimer, the term of this patent is extended or adjusted under 35 U.S.C. 154(b) by 0 days.

(21) Appl. No.: 09/352,570

(22) Filed: Jul. 13, 1999

(51) Int. Cl.$^7$ ............................................... G01N 33/53
(52) U.S. Cl. ........................ 435/7.2; 435/7.1; 435/7.8; 435/7.6
(58) Field of Search ........................... 435/7.6, 7.1, 7.2, 435/7.8

(56) References Cited

PUBLICATIONS

Mendelsohn et al., "Mechanisms of Estrogen Action in the Cardiovascular System," Nobel Symposium (Jun. 30, 1999).
Iafrati et al., "Estrogen Inhibits the Vascular Injury Response in Estrogen Receptor α–deficient Mice", *Nature Medicine*, vol. 3, No. 5, pps. 545–548, 1997.
Lindner et al., "Increased Expression of Estrogen Receptor–β mRNA in Male Blood Vessels After Vascular Injury", *Circulation. Research.*, 83: 224–229, 1998.
Elledge, "Mitotic Arrest: Mad2 Prevents Sleepy from Waking Up the APC", *Science*, vol. 279, pps. 999–1000, 1998.

*Primary Examiner*—Michael Pak
(74) *Attorney, Agent, or Firm*—Paul T. Clark; Clark & Elbing LLP (57) ABSTRACT

The invention provides a method for assaying compounds that affect cell division by determining the interaction between estrogen receptor ERβ and MAD2, a cell cycle checkpoint protein.

4 Claims, 5 Drawing Sheets

```
EC1.txt    1:-----------------CGGGAGCAAGGCATCACCTTGCGCGGGAGCGCCGAGATCGTG 42
mad2.txt   1:ATGGCGCTGCAGCTCTCCCGGGAGCAGGGAATCACCCTGCGCGGGAGCGCCGAAATCGTG 60
                              ******* ** ****** ***************** *****

EC1.txt   43:GCCGAGTTCTTCTCATTTGGTATCAACAGTATTTTATATCAGCGTGGCATATATCCATCG 102
mad2.txt  61:GCCGAGTTCTTCTCATTCGGCATCAACAGCATTTTATATCAGCGTGGCATATATCCATCT 120
             ***************** ** ******** ******************************

EC1.txt  103:GAAACCTTTACTCGAGTGCAGAAATATGGACTCACCTTGCTTGTAACTACTGATCCTGAG 162
mad2.txt 121:GAAACCTTTACTCGAGTGCAGAAATACGGACTCACCTTGCTTGTAACTACTGATCTTGAG 180
             ************************** *************************** ****

EC1.txt  163:CTCATAAAATACCTAAATAATGTGGTGGATCAACTAAAAGAATGGTTATACAAGTGTTCA 222
mad2.txt 181:CTCATAAAATACCTAAATAATGTGGTGGAACAACTGAAAGATTGGTTATACAAGTGTTCA 240
             ***************************** ***** ***** *****************

EC1.txt  223:GTTCAGAAACTGGTGGTAGTCATCTCAAATATTGAAAGTGGAGAGGTCCTTGAAAGATGG 282
mad2.txt 241:GTTCAGAAACTGGTTGTAGTTATCTCAAATATTGAAAGTGGTGAGGTCCTGGAAAGATGG 300
             ************** ***** ******************** ******** *********

EC1.txt  283:CAGTTTGATATTGAGTGTGACAAGACTGCAAAAGATGACAGTGCACCCAGAGAAAAGTCT 342
mad2.txt 301:CAGTTTGATATTGAGTGTGACAAGACTGCAAAAGATGACAGTGCACCCAGAGAAAAGTCT 360
             ************************************************************

EC1.txt  343:CAGAAAGCTATCCAAGATGAAATCCGTTCAGTGATCAGACAGATCACAGCTACAGTAACA 402
mad2.txt 361:CAGAAAGCTATCCAGGATGAAATCCGTTCAGTGATCAGACAGATCACAGCTACGGTGACA 420
             ************** *************************************** ** ***

EC1.txt  403:TTTCTGCCACTGTTGGAAGTTTCTTGTTCATTTGATCTCCTCATTTATACAGACAAAGAT 462
mad2.txt 421:TTTCTGCCACTGTTGGAAGTTTCTTGTTCATTTGATCTGCTGATTTATACAGACAAAGAT 480
             ************************************** ** *****************

EC1.txt  463:CTGGTTGTNCCTGAGAAATGGGAAGA-TCNGGACCACAGTTCATTACCAATTCTGAAGAA 521
mad2.txt 481:TTGGTTGTACCTGAAAAATGGGAAGAGTCGGGACCACAGTTTATTACCAATTCTGAGGAA 540
             ****** ***** ************ ** ********* ***************** ***

EC1.txt  522:GTTCGTCTTCGTTCATTCACTACTACAATTCACAAAGTAAATAGCATGGTAGCCTACAAA 581
mad2.txt 541:GTGCGCCTTCGTTCATTTACTACTACAATCCACAAAGTAAATAGCATGGTGGCCTACAAA 600
             ** ** *********** *********** *********************** ********

EC1.txt  582:ATTCCTGTCCATGACTGA                                          599
mad2.txt 601:ATTCCTGTCAATGACTGA                                          618
             ********* ********
```

Fig. 2A

```
EC-1:     1 REQGITLPGSAEIVAEFFSFGINSILYQRGIYPSETFTRVQKYGLTLLVTTDPELIKYLN  60
            REQGITL GSAEIVAEFFSFGINSILYQRGIYPSETFTRVQKYGLTLLVTTD ELIKYLN
hsMAD2:   7 REQGITLRGSAEIVAEFFSFGINSILYQRGIYPSETFTRVQKYGLTLLVTTDLELIKYLN  66

EC-1:    61 NVVDQLKEWLYKCSVQKLVVVISNIESGEVLERWQFDIECDKTAKDDSAPRQKSQKAIQD 120
            NVV+QLK+WLYKCSVQKLVVVISNIESGEVLERWQFDIECDKTAKDDSAPR+KSQKAIQD
hsMAD2:  67 NVVEQLKDWLYKCSVQKLVVVISNIESGEVLERWQFDIECDKTAKDDSAPREKSQKAIQD 126

EC-1:   121 EIRSVIRHITATVTFLPLLEVSCSFDLLIYTDKDLVVPEKWEXSGPQFITNSEELRLRSF 180
            EIRSVIR ITATVTFLPLLEVSCSFDLLIYTDKDLVVPEKWE SGPQFITNSEE+RLRSF
hsMAD2: 127 EIRSVIRQITATVTFLPLLEVSCSFDLLIYTDKDLVVPEKWEESGPQFITNSEEVRLRSF 186

EC-1:   181 TTTIHKVNSMVAYKIPVHD 199
            TTTIHKVNSMVAYKIPV+D
hsMAD2: 187 TTTIHKVNSMVAYKIPVND 205
```

| BD | AD | HIS | β-Gal |
|---|---|---|---|
| EC1 | /- | - | - |
| EC1 | /AD | - | - |
| EC1 | /mERβ516-1458 | + | + |
| EC1 | /mERβ | + | + |
| BD | /mERβ516-1458 | - | - |
| mERα | /mERβ516-1458 | + | + |
| mERβ1-622 | /EC1 | + | + |
| mERβ1-516 | /EC1 | - | - |
| mERβ1 516-641 | /EC1 | | |
| mERβ1-622 | /AD | - | - |
| mERβ1-516 | /AD | - | - |
| mERβ | /EC1 | + | + |
| BD | /EC1 | - | - |

SEQUENCE LISTING

<160> NUMBER OF SEQ ID NOS: 4

<210> SEQ ID NO 1
<211> LENGTH: 618
<212> TYPE: DNA
<213> ORGANISM: Homo sapiens
<220> FEATURE:
<221> NAME/KEY: CDS
<222> LOCATION: (1)...(618)

<400> SEQUENCE: 1

```
atg gcg ctg cag ctc tcc cgg gag cag gga atc acc ctg cgc ggg agc      48
Met Ala Leu Gln Leu Ser Arg Glu Gln Gly Ile Thr Leu Arg Gly Ser
 1               5                  10                  15 gcc gaa atc gtg gcc gag ttc ttc tca ttc ggc atc aac agc att tta      96
Ala Glu Ile Val Ala Glu Phe Phe Ser Phe Gly Ile Asn Ser Ile Leu
                20                  25                  30 tat cag cgt ggc ata tat cca tct gaa acc ttt act cga gtg cag aaa     144
Tyr Gln Arg Gly Ile Tyr Pro Ser Glu Thr Phe Thr Arg Val Gln Lys
             35                  40                  45 tac gga ctc acc ttg ctt gta act act gat ctt gag ctc ata aaa tac     192
Tyr Gly Leu Thr Leu Leu Val Thr Thr Asp Leu Glu Leu Ile Lys Tyr
         50                  55                  60 cta aat aat gtg gtg gaa caa ctg aaa gat tgg tta tac aag tgt tca     240
Leu Asn Asn Val Val Glu Gln Leu Lys Asp Trp Leu Tyr Lys Cys Ser
 65                  70                  75                  80 gtt cag aaa ctg gtt gta gtt atc tca aat att gaa agt ggt gag gtc     288
Val Gln Lys Leu Val Val Val Ile Ser Asn Ile Glu Ser Gly Glu Val
                 85                  90                  95 ctg gaa aga tgg cag ttt gat att gag tgt gac aag act gca aaa gat     336
Leu Glu Arg Trp Gln Phe Asp Ile Glu Cys Asp Lys Thr Ala Lys Asp
                100                 105                 110 gac agt gca ccc aga gaa aag tct cag aaa gct atc cag gat gaa atc     384
Asp Ser Ala Pro Arg Glu Lys Ser Gln Lys Ala Ile Gln Asp Glu Ile
            115                 120                 125 cgt tca gtg atc aga cag atc aca gct acg gtg aca ttt ctg cca ctg     432
Arg Ser Val Ile Arg Gln Ile Thr Ala Thr Val Thr Phe Leu Pro Leu
        130                 135                 140 ttg gaa gtt tct tgt tca ttt gat ctg ctg att tat aca gac aaa gat     480
Leu Glu Val Ser Cys Ser Phe Asp Leu Leu Ile Tyr Thr Asp Lys Asp
145                 150                 155                 160 ttg gtt gta cct gaa aaa tgg gaa gag tcg gga cca cag ttt att acc     528
Leu Val Val Pro Glu Lys Trp Glu Glu Ser Gly Pro Gln Phe Ile Thr
                165                 170                 175 aat tct gag gaa gtg cgc ctt cgt tca ttt act act aca atc cac aaa     576
Asn Ser Glu Glu Val Arg Leu Arg Ser Phe Thr Thr Thr Ile His Lys
            180                 185                 190 gta aat agc atg gtg gcc tac aaa att cct gtc aat gac tga             618
Val Asn Ser Met Val Ala Tyr Lys Ile Pro Val Asn Asp *
        195                 200                 205
```

<210> SEQ ID NO 2
<211> LENGTH: 199
<212> TYPE: PRT
<213> ORGANISM: Homo sapiens

<400> SEQUENCE: 2

```
Arg Glu Gln Gly Ile Thr Leu Arg Gly Ser Ala Glu Ile Val Ala Glu
 1               5                  10                  15

Phe Phe Ser Phe Gly Ile Asn Ser Ile Leu Tyr Gln Arg Gly Ile Tyr
                20                  25                  30
```

```
Pro Ser Glu Thr Phe Thr Arg Val Gln Lys Tyr Gly Leu Thr Leu Leu
        35                  40                  45

Val Thr Thr Asp Leu Glu Leu Ile Lys Tyr Leu Asn Asn Val Val Glu
 50                  55                  60

Gln Leu Lys Asp Trp Leu Tyr Lys Cys Ser Val Gln Lys Leu Val Val
 65                  70                  75                  80

Val Ile Ser Asn Ile Glu Ser Gly Val Leu Glu Arg Trp Gln Phe
                85                  90                  95

Asp Ile Glu Cys Asp Lys Thr Ala Lys Asp Asp Ser Ala Pro Arg Glu
                100                 105                 110

Lys Ser Gln Lys Ala Ile Gln Asp Glu Ile Arg Ser Val Ile Arg Gln
                115                 120                 125

Ile Thr Ala Thr Val Thr Phe Leu Pro Leu Leu Glu Val Ser Cys Ser
        130                 135                 140

Phe Asp Leu Leu Ile Tyr Thr Asp Lys Asp Leu Val Val Pro Glu Lys
145                 150                 155                 160

Trp Glu Glu Ser Gly Pro Gln Phe Ile Thr Asn Ser Glu Glu Val Arg
                165                 170                 175

Leu Arg Ser Phe Thr Thr Thr Ile His Lys Val Asn Ser Met Val Ala
                180                 185                 190

Tyr Lys Ile Pro Val Asn Asp
        195
```

<210> SEQ ID NO 3
<211> LENGTH: 600
<212> TYPE: DNA
<213> ORGANISM: Ovis aries
<220> FEATURE:
<221> NAME/KEY: CDS
<222> LOCATION: (1)...(600)

<400> SEQUENCE: 3

```
cgg gag caa ggc atc acc ttg cgc ggg agc gcc gag atc gtg gcc gag      48
Arg Glu Gln Gly Ile Thr Leu Arg Gly Ser Ala Glu Ile Val Ala Glu
 1               5                  10                  15 ttc ttc tca ttt ggt atc aac agt att tta tat cag cgt ggc ata tat      96
Phe Phe Ser Phe Gly Ile Asn Ser Ile Leu Tyr Gln Arg Gly Ile Tyr
                 20                  25                  30 cca tcg gaa acc ttt act cga gtg cag aaa tat gga ctc acc ttg ctt     144
Pro Ser Glu Thr Phe Thr Arg Val Gln Lys Tyr Gly Leu Thr Leu Leu
         35                  40                  45 gta act act gat cct gag ctc ata aaa tac cta aat aat gtg gtg gat     192
Val Thr Thr Asp Pro Glu Leu Ile Lys Tyr Leu Asn Asn Val Val Asp
 50                  55                  60 caa cta aaa gaa tgg tta tac aag tgt tca gtt cag aaa ctg gtg gta     240
Gln Leu Lys Glu Trp Leu Tyr Lys Cys Ser Val Gln Lys Leu Val Val
 65                  70                  75                  80 gtc atc tca aat att gaa agt gga gag gtc ctt gaa aga tgg cag ttt     288
Val Ile Ser Asn Ile Glu Ser Gly Glu Val Leu Glu Arg Trp Gln Phe
                 85                  90                  95 gat att gag tgt gac aag act gca aaa gat gac agt gca ccc aga gaa     336
Asp Ile Glu Cys Asp Lys Thr Ala Lys Asp Asp Ser Ala Pro Arg Glu
                100                 105                 110 aag tct cag aaa gct atc caa gat gaa atc cgt tca gtg atc aga cag     384
Lys Ser Gln Lys Ala Ile Gln Asp Glu Ile Arg Ser Val Ile Arg Gln
                115                 120                 125 atc aca gct aca gta aca ttt ctg cca ctg ttg gaa gtt tct tgt tca     432
Ile Thr Ala Thr Val Thr Phe Leu Pro Leu Leu Glu Val Ser Cys Ser
        130                 135                 140
```

```
ttt gat ctc ctc att tat aca gac aaa gat ctg gtt gta cct gag aaa    480
Phe Asp Leu Leu Ile Tyr Thr Asp Lys Asp Leu Val Val Pro Glu Lys
145                 150                 155                 160 tgg gaa gag tcc gga cca cag ttc att acc aat tct gaa gaa gtt cgt    528
Trp Glu Glu Ser Gly Pro Gln Phe Ile Thr Asn Ser Glu Glu Val Arg
                165                 170                 175 ctt cgt tca ttc act act aca att cac aaa gta aat agc atg gta gcc    576
Leu Arg Ser Phe Thr Thr Thr Ile His Lys Val Asn Ser Met Val Ala
            180                 185                 190 tac aaa att cct gtc cat gac tga                                    600
Tyr Lys Ile Pro Val His Asp *
        195

<210> SEQ ID NO 4
<211> LENGTH: 199
<212> TYPE: PRT
<213> ORGANISM: Ovis aries

<400> SEQUENCE: 4

Arg Glu Gln Gly Ile Thr Leu Arg Gly Ser Ala Glu Ile Val Ala Glu
1               5                   10                  15

Phe Phe Ser Phe Gly Ile Asn Ser Ile Leu Tyr Gln Arg Gly Ile Tyr
                20                  25                  30

Pro Ser Glu Thr Phe Thr Arg Val Gln Lys Tyr Gly Leu Thr Leu Leu
            35                  40                  45

Val Thr Thr Asp Pro Glu Leu Ile Lys Tyr Leu Asn Asn Val Val Asp
        50                  55                  60

Gln Leu Lys Glu Trp Leu Tyr Lys Cys Ser Val Gln Lys Leu Val Val
65                  70                  75                  80

Val Ile Ser Asn Ile Glu Ser Gly Glu Val Leu Glu Arg Trp Gln Phe
                85                  90                  95

Asp Ile Glu Cys Asp Lys Thr Ala Lys Asp Asp Ser Ala Pro Arg Glu
                100                 105                 110

Lys Ser Gln Lys Ala Ile Gln Asp Glu Ile Arg Ser Val Ile Arg Gln
            115                 120                 125

Ile Thr Ala Thr Val Thr Phe Leu Pro Leu Leu Glu Val Ser Cys Ser
        130                 135                 140

Phe Asp Leu Leu Ile Tyr Thr Asp Lys Asp Leu Val Val Pro Glu Lys
145                 150                 155                 160

Trp Glu Glu Ser Gly Pro Gln Phe Ile Thr Asn Ser Glu Glu Val Arg
                165                 170                 175

Leu Arg Ser Phe Thr Thr Thr Ile His Lys Val Asn Ser Met Val Ala
            180                 185                 190

Tyr Lys Ile Pro Val His Asp
        195
```

METHOD FOR ASSAYING COMPOUNDS AFFECTING CELL DIVISION USING ESTROGEN RECEPTOR BETA (ERβ) AND MITOSIS ARREST DEFICIENT 2 (MAD2)

STATEMENT AS TO FEDERALLY SPONSORED RESEARCH

The invention was made, in part with funding from the National Institutes of Health, grant HL56069. The government may have certain rights in the invention.

BACKGROUND OF THE INVENTION

Estrogen receptor beta (ER beta), first reported in 1996, is the second estrogen receptor cloned. Like the original estrogen receptor (ER alpha), ER beta has the ability to act as a transcription factor by binding estrogen. The amino-terminal domain of ER beta differs considerably from that of ER alpha, while the DNA binding domain is highly homologous, and the hormone binding and carboxyl-terminal domains are partially homologous, to ER alpha.

While ER beta, like ER alpha, binds hormone and modulates changes in transcription, a fundamental question has been whether ER beta possesses additional function(s). ER beta has been postulated to play a role in the cardiovascular system and may be involved in the vascular protective effects of estrogen (Iafrati et al., Nat. Med. 3:545–8, 1997). An estrogen receptor alpha knock-out mouse was still protected against vascular injury upon estrogen administration. This implied another way for estrogen to exert its protective effects and led to the discovery of ER beta in blood vessels. ER beta was discovered in the rat prostate, originally, and was then found to be expressed in blood vessels, including the blood vessels of the ER knock-out mouse. Furthermore, if a blood vessel of a male rat is injured, regrowth of endothelial and smooth muscle cells occurs as that injury repairs itself, accompanied by a dramatic increase in ER beta expression at the leading edge of cells as they grow back. There is no change in the expression of ER alpha in this setting (Lindner et al., Circ. Res. 83:224–9, 1998).

SUMMARY OF THE INVENTION

I have discovered, unexpectedly, that ER beta interacts with Mitosis Arrest Deficient 2 (MAD2), a cell cycle checkpoint protein. Accordingly, the invention features a novel method for assaying compounds that affect cell division by determining the interaction between estrogen receptor (ER beta) and MAD2

In more detail, the invention features a method for determining whether a test compound is potentially capable of affecting cell division, by: a) contacting the test compound with ER beta and MAD2, or binding fragments thereof, under conditions in which ER beta and MAD2 or fragments have formed, or are able to form, a complex; and b) determining whether the test compound affects the ER beta/MAD2 complex or complex formation, as an indication that the test compound is potentially capable of affecting cell division.

In preferred embodiments of the invention, the assay may be conducted in vitro or in vivo. In other preferred embodiments of the invention, a yeast two-hybrid system, a GST-fusion protein interaction assay, fluorescence spectroscopy, or biomolecular interaction analysis using, for example, chip technology, may be used to assay the test compound.

By "test compound" is meant any chemical compound, be it naturally-occurring or artificially-derived. Test compounds may include, for example, peptides, polypeptides, synthesized organic molecules, naturally occurring organic molecules, and nucleic acid molecules.

By "affecting" is meant changing, either by increase or decrease.

By "cell division" is meant a process by which a cell replicates itself. As defined in this invention, cell division may include any stage in the cell cycle, such as mitosis, $G_1$, S phase, and $G_2$.

By "determining" is meant analyzing the effect of a test compound on the test system. The readout of the analysis may be disruption or enhancement of the interaction between ER beta and MAD2, as well as measures of cell division. The means of analyzing may include, for example, yeast two-hybrid assays, GST fusion protein interaction, immunoprecipitation, fluorescence spectroscopy, biomolecular interaction analysis, and other methods known to those skilled in the art.

The invention provides a means of identifying test compounds that affect cell division. This is particularly useful since abnormalities in cell division have been associated with a variety of conditions associated with cell proliferative diseases. Thus, compounds that affect cell proliferation may be used in therapy, prevention, or diagnosis of such diseases.

Other features and advantages of the invention will be apparent from the following detailed description and from the claims.

BRIEF DESCRIPTION OF THE DRAWINGS

FIG. 2A Alignment of nucleotide sequences of EC1 SEQ ID NO:3 and hsMAD2. SEQ ID NO:1

DETAILED DESCRIPTION OF THE INVENTION

I have discovered a novel interaction between the estrogen receptor ER beta and a protein called MAD2, which is a cell cycle checkpoint protein. This is a surprising finding and has interesting scientific and practical implications.

Function of the MAD2/ER Beta Interaction

To address the question as to the function of the ER beta/MAD2 interaction, one can begin with an overview of the information previously known about MAD2. MAD2 is a member of a family of proteins that are involved in cell surveillance of the spindle assembly checkpoint during cell division (Elledge, Science 279:999–1000, 1998). The checkpoint blocks separation of sister chromatids in the dividing cell until the two sister chromatids are attached to the opposite poles of the spindle. Unless each sister chromatid is aligned correctly through its link to its connecticore, cell division will not take place. On page 1000 of the Science article, Elledge states: "Although pleasing, this model contains several unresolved but important details. For example, is the spindle checkpoint transiently activated in every cell cycle or only in response to spindle perturbation?"

Confocal immunofluorescence microscopy shows that ER beta is localized with MAD2 at the kinetochore when the cell is in prometaphase. Therefore, ER beta is part of the spindle checkpoint and the ER beta/MAD2 complex may play a physiological role in every cell during the cell cycle. This confirms other protein-protein interaction data shown herein and also reveals the presence of ER beta in the kinetochore, a discovery which is totally unexpected and is the first instance of the localization of a steroid hormone receptor to the cell division molecular apparatus. The results presented herein indicate that the interaction between ER beta and MAD2 affects cell division.

Drug Screening

As is stated in the Summary of the Invention, above, compounds that affect the interaction of ER beta with MAD2 are potential cell cycle-affecting drugs.

Cell-Based Assays

One method for screening test compounds can employ a cellular system, in which as the components are present inside a cell. The test compound, at concentrations of approximately $10^{-12}$–$10^{-5}$ M, is also placed in the cell, and interacts with, or fails to interact with, ER beta and MAD2 in the cellular environment. Yeast and mammalian two hybrid systems are examples of such systems, and are commercially available (Clontech, Palo Alto, Calif. Promega, Madison, Wis.) or can be readily developed to suit specific screening applications. Cellular systems have the potential advantage that other molecules, present in a living cell, might participate in the interaction. Test compounds that affect the interaction between ER beta and MAD2 in such systems, therefore, are more likely to be of physiological relevance.

Non-Cell-Based Assays

One straightforward readout for the effect of a test compound on the ER beta/MAD2 interaction is to employ an in vitro system in which one or both of ER beta or MAD2 is linked to a fluorophore that only fluoresces, or fluoresces at a different wavelength, if ER beta and MAD2 interact with each other. Thus, fluorescence at a given wavelength occurs only if the conformation of one of the pair is changed because of its interaction with the other member of the pair; one can therefore determine, by detecting the intensity or wavelength of the fluorescence, the extent to which the test compound influenced, or failed to influence, the conformational change that accompanies complex formation. Fluorophores may include, for example, synthetic compounds or proteins such as green or blue fluorescent proteins or phycobiliproteins.

Another non-cell based system for the effect of a test compound on the ER beta/MAD2 interaction is the biomolecular interaction analysis (BIA) system, which examines the interaction of molecules in real time. BIA is an affinity-based biosensor technology that relies on the optical phenomenon of surface plasmon resonance (SPR), which detected changes in the refractive index of a solution close to the surface of a sensor chip. Either one of ER beta or MAD2 can be immobilized in a suitable matrix on the sensor chip, which forms one wall of a micro-flow cell. Sample, such as cell extract containing the other interactant (MAD2 or ER beta), and a test compound can then be injected over the surface in a controlled flow. Changes in surface concentration resulting from a change in the interaction between MAD2 and ER beta is detected as a SPR signal which is expressed in resonance units. An advantage of BIA technology is that complex interactions, involving multimeric complexes, may be examined. The concentrations of the test compounds may range from approximately $10^{-12}$–$10^{-5}$ M.

Therapeutic Methods

The invention contemplates two broad categories of therapeutic methods based on the present discovery: administration of compounds (drugs) identified using the above-described screening methods, and gene therapy using DNA encoding ER beta or MAD2, or fragments of one of these proteins. ER beta/MAD2-based therapies identified according to the present invention may be used alone, or as an adjunct to other therapies, such as, for example, with vascular endothelial growth factor for therapeutic angiogenesis.

Drug Treatment

Two main classes of drugs can be identified by the above-described screening methods: 1) drugs that inhibit the binding of ER beta to MAD2, and 2) drugs that promote or enhance such binding.

Enhancement of the ER Beta/MAD2 Interaction

Assuming that formation of the ER beta/MAD2 complex acts, in vivo, as a brake on the cell cycle; i.e., that the interaction slows cell proliferation, drugs that promote the formation of the complex are potentially useful in the treatment of any of the many known hyperproliferative disorders, including cancer, psoriasis, excessive scar tissue formation, atherosclerosis, restenosis following vascular injury, and adhesion formation. Such anti-proliferative drugs are administered by any of the routes by which other known anti-proliferatives are administered; e.g., orally or intravenously, admixed with any appropriate pharmaceutically acceptable carrier. In some cases, such as widely diffused Ad cancer, systemic administration will be preferred. In other instances, e.g., to inhibit vein or artery graft restenosis or to treat a site-confined solid tumor, the drug will be delivered locally, to the site of hyperproliferation, by any appropriate means, e.g., direct injection or delivery via catheter. When the site of hyperproliferation is the skin, e.g., in the case of psoriasis, the drug can be applied topically in the form of a cream or ointment. Should pulmonary administration be required, the drug can be administered by aerosol.

Promotion of complex formation that slows cell growth might also treat cardiovascular disease, because the interaction might "time" the repair process in the vessel, since ER beta is unregulated during the repair process. Further, with respect to cancer, the role of ER beta in interacting with MAD2 may be to increase the fidelity and sensitivity of MAD2's surveillance for aberrantly aligned chromatids and for cells that are aberrant in their chromosomal segregation. Thus, ER beta would be up-regulated in times of rapid proliferation, to eliminate aberrant cells that arise during such an increase in proliferation.

Inhibition of the ER Beta/MAD2 Interaction

Assuming, still, that the formation of the ER beta/MAD2 complex acts, in vivo, as a brake on the cell cycle, drugs that interfere with, or block the formation of, the complex are potentially useful in the treatment of any of the known medical condition in which increased cell growth is desired. Examples are wound healing; vascular regrowth or Ad angiogenesis following a myocardial infarction or other disorders in which tissues are underperfused; and hepatic regrowth following transplant of a piece of donor liver. Administration is as described above for complex-promoting drugs.

With respect to the possibility that the ER beta/MAD2 interaction facilitates, rather than slows, cell division, this is less likely given the present data since the ER beta knock-out mouse remains well protected by estrogen. If the complex enhanced cell proliferation, one would predict less of an injury in the ER beta knockout animal, and in fact we see the same level of injury and the same degree of protection by estrogen. Nonetheless, enhancement of cell proliferation by the complex cannot be ruled out, and if it is the case, promotion of complex formation is potentially a therapeutic approach to the treatment of diseases, e.g. cardiovascular diseases and wound-healing, in which such enhanced cellular proliferation is desired. Conversely, inhibition of complex formation would provide a therapeutic approach to the treatment of hyperproliferative disorders such as cancer and psoriasis.

Nucleic Acid Therapy

Just as drugs (generally, small organic molecules) identified in the screening assays of the invention can either act as promotors or inhibitors of the ER beta/MAD2 complex, nucleic acid molecules can serve either of those two functions.

Several nucleic acid-based strategies can be employed to enhance or interfere with the ER beta/MAD2 interaction. All of these approaches can employ any of the known methodologies for delivering nucleic acids (usually DNA) to cells and tissues. These include the use of viral vectors, derived, for example, from retroviruses, adenoviruses, adeno-associated viruses, and lentiviruses, plasmids packaged in liposomes or linked to cationic polymers, and the use of naked i.e., uncomplexed, charged DNA.

Enhancement of the ER Beta/MAD2 Interaction

Several classes of nucleic acid molecules can enhance ER beta/MAD2 complex formation, ultimately resulting in an increased amount of the complex within cells, or in the formation of tighter complexes (shifting the complex formation to the right, favoring complex formation over dissociation in the in vivo equilibrium).

The most straightforward nucleic acid-based strategy for increasing the amount of ER beta/MAD2 complex is to provide expressible nucleic acid encoding one (or both) of the proteins. For example, in some clinical situations the factor that limits the amount of complex present is an inadequate amount of one of the two proteins; that protein is, thus, supplemented by providing to the cells nucleic acid encoding it. As is described above, the expressible DNA is provided using any of the known, available methods, e.g., retroviral or other viral vectors.

It is also possible that a biologically active complex can be formed from the ER beta and MAD2 that are not full-length. Thus, nucleic acid encoding the binding regions of these proteins can be used in the complex-enhancing methods of the invention.

Inhibition of the ER Beta/MAD2 Interaction

As is mentioned above, some medical conditions may be treated by inhibiting the complex formation of ER beta with MAD2. This can be accomplished by administration of a nucleic acid molecule encoding a fragment of one of the proteins that is capable of binding to the other protein, or of a sequence closely related to the binding domain that disrupts the interaction, thus competitively inhibiting the undesired protein-protein interaction. The use of anti-sense RNA is also contemplated as an approach that can interfere with the ER beta/MAD2 interaction.

Diagnostic Applications

Mutants or allelic variants of ER beta or MAD2 that have an altered level of interaction with the other are likely to exist. Accordingly, a screening method to identify people who are more or less susceptible to certain hyperproliferative diseases can be developed. Thus, for example, there may be men who develop prostate cancer because they have an allelic variant of ER beta with an altered binding domain for MAD2, rendering the interaction between the two less favorable or less tight. That variation would be easily screened for, to detect men at higher risk for prostate cancer. Conversely there might be men who have allelic variants that provide greater protection from prostate cancer.

EXAMPLES

Yeast Two-Hybrid Assays
Library Screening

The full-length coding region of mouse ER beta (mERβ) was cloned in frame into the EcoRI site of the Gal4 DNA binding domain (BD) vector, pGBT9, to yield the construct mERβ/BD. mERβ/BD and an ovine pulmonary artery endothelial cell (immortalized, P11) library (constructed using the Two-hybrid cDNA Library Construction Kit, Clontech, Palo Alto, Calif., USA), cloned into the Gal4 DNA activating domain (AD) vector pGAD10, were transformed into *Saccharomyces cerevisiae* strain Y190 (MAT a, ura3-re, his3-200, lys2-801, ade2-101, trp1-901, leu2-3112, gal4Δ, gal80Δ, cyhr2, LYS2:: GAL1UAS-HIS2TATA-HIS2, URA3::GAL1UAS-GAL1TATA-lacZ; Clontech, Palo Alto, Calif.) using the lithium acetate method.

Polypeptides interacting with mERβ/BD were detected by their ability to reconstitute the GAL4 transcription factor and activate transcription of HIS3 and LacZ reporter genes. *S. cerevisiae* colonies able to grow on media lacking histidine were assayed for β-galactosidase activity using a colony lift filter assay.

Colonies were lifted onto MSI NitroPure nitrocellulose filters (MSI, Westoboro, Mass., USA) which were then submerged in liquid nitrogen for 15 seconds, placed on Whatman #5 paper presoaked in Z-buffer (60 mM $Na_2HPO_4.7H_2O$, 40 mM $NaH_2PO_4.H_2O$, 10 mM Kcl, 1 mM $MgSO_4$, $7H_2O$, 50 mM β-mercaptoethanol, pH7.0), and incubated at 37° for up to 12 hours. PGAD10 plasmids from His+, LacZ+ colonies were isolated and the library cDNA insert sequenced. Four double transformation individual plasmids were reintroduced into *S. cerevisiae* strain Y190 by the lithium acetate method, and reporter activation assayed as above.

Figure 1A:
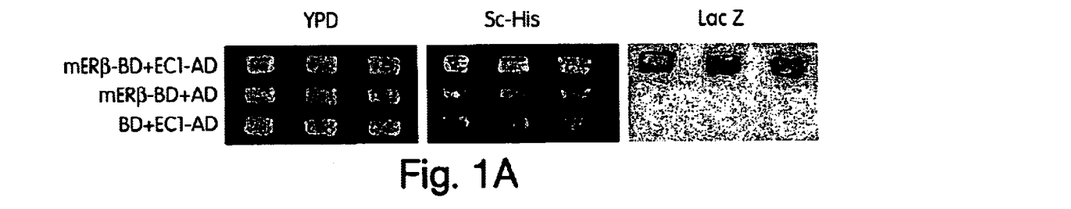
FIG. 1A Interaction of mERβ with EC1 in yeast.
Figure 1B:
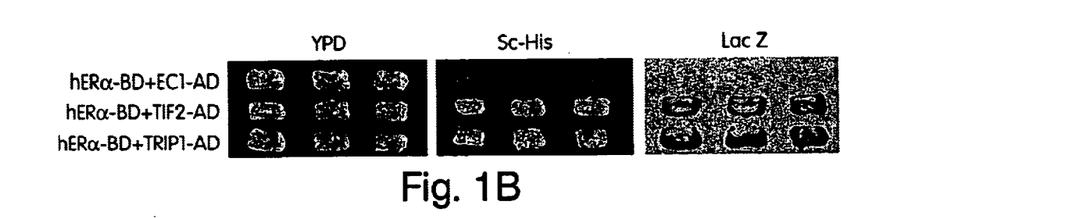
FIG. 1B Interaction of hERα with EC1 in yeast.

Screening of the ovine library yielded clone EC1. FIG. 1 shows the definitive interaction between the binding domain of ER beta and clone EC1. Yeast strain Y190 was transformed with mERβ/BD in combination with EC1/AD and GalAD respectively and plated on Sc-His (synthetic complete medium, minus histidine) and YPD (yeast extract, peptone, dextrose) plates (FIG. 1A). Positive interaction of mERβ/BD with EC1/AD was seen in the presence, as well as in the absence, of estrogen. Yeast strain Y190 was also transformed with human ER alpha (hERα)/BD in combination with EC1/AD, hERα/BD and Trip 1/AD and plated on Sc-His and YPD plates. Positive interaction of hERα/BD with hERα/GalBD and Trip 1/GalAD was seen only in the presence of estrogen. Colony lift β-Galactosidase assays were also performed with yeasts from the YPD plate in both FIG. 1A and 1B. TIF2 and TRIP1 homologs were found previously by screening a human heart library with mERβ as bait. Thus, these results indicate that the interaction between EC1 and ER beta is estrogen independent, while that between EC1 and ER alpha is estrogen dependent. This implies a new function for ER beta that may be separated from its estrogen binding function.

Example 2

The ER-Beta/MAD2 Interaction

Figure 2B:
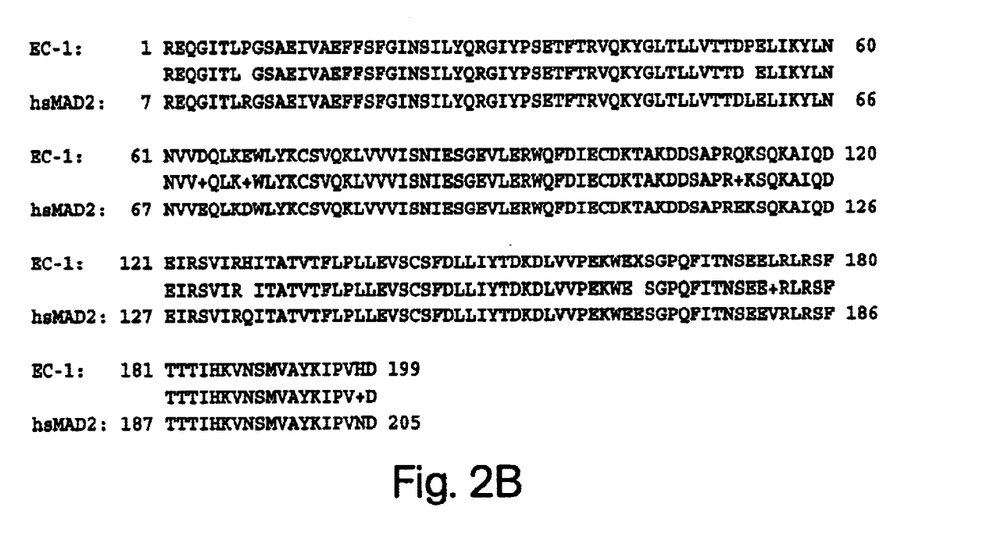
FIG. 2B Alignment of amino acid sequences of EC1 SEQ ID NO:4 and hsMAD2. SEQ ID NO:2

Sequencing of clone EC1 revealed that it was almost identical to a well-known and a well-studied cDNA called MAD2 (FIG. 2). Alignment of the EC1 nucleotide sequence SEQ ID NO:3, with that of *homo sapiens* MAD2 (hsMAD2) SEQ ID NO:1, revealed 93% identity. Identical nucleotides are marked with asterisks (FIG. 2A). Similarly, alignment of the amino acid sequence of EC1 SEQ ID NO:4 with that of hsMAD2 SEQ ID NO:2, revealed 95% identity. Identities are shown by the abbreviation of the corresponding amino acid, similarities by + symbols, and amino acid mismatch by a gap (FIG. 2B). The difference between EC1 and MAD2 is likely to be due to inter-species variation because EC1 was obtained from sheep and the particular MAD2 that was used for the sequence comparison was of human origin.

Experiments that showed that ER beta and MAD2 form complexes with one another were then carried out. These results were unexpected; MAD2 would not have been expected to interact with ER beta based on any prior knowledge about either protein.

Figure 3A:
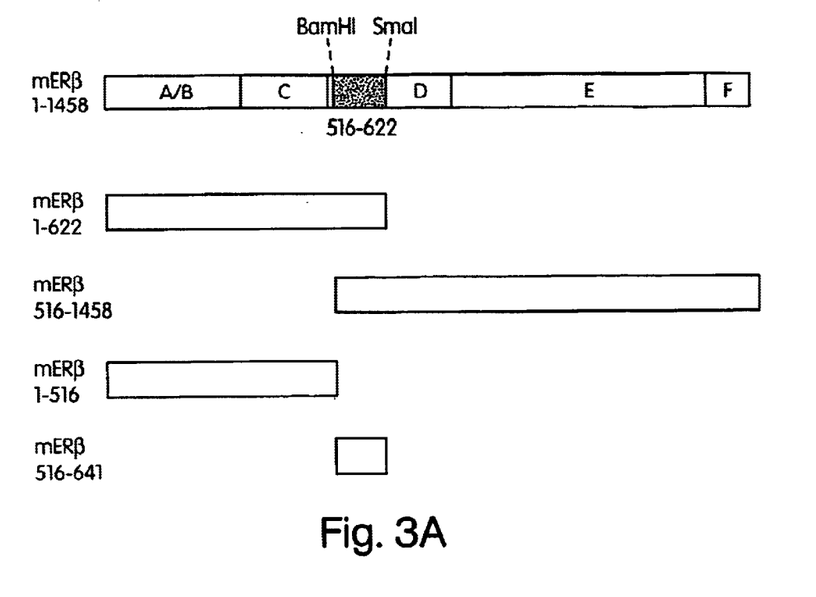
FIG. 3A Schematic diagram of mERβ cDNA showing domains and the mERβ mutants that were constructed to correspond to the domains.
Figure 3B:
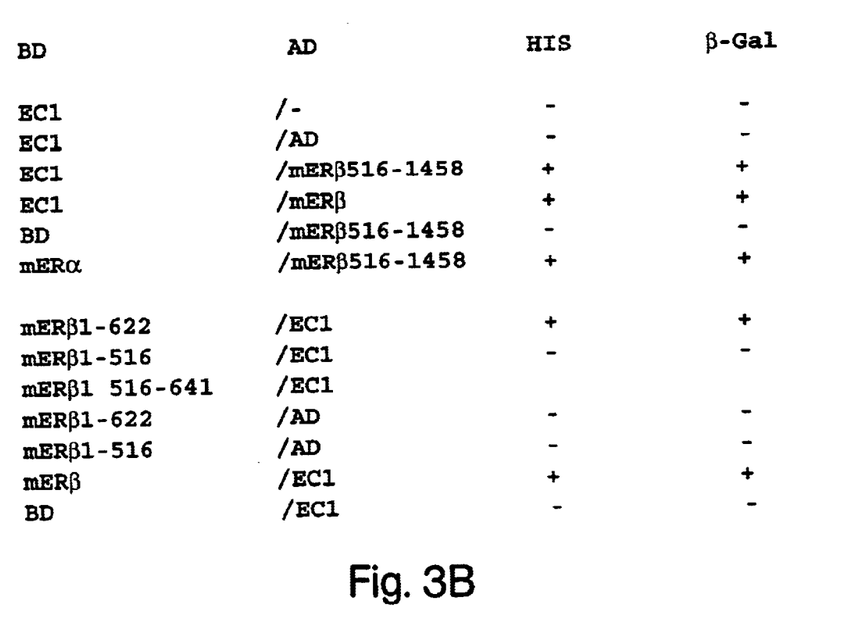
FIG. 3B Summary of HIS and β-Galactosidase reporter activation for the mERβ/GalBD and mERβ/GalAD mutants cotransformed in Y190 with EC1/GalAD or EC1/GalBD respectively.

FIG. 3 is a schematic diagram summarizing the MAD2/ER beta interaction. A series of truncations were made and tested in the two hybrid system to determine whether ER beta/MAD2 interactions are maintained or lost with a given deletion.

The N-terminal mERβ truncation mutants, mERβ 1-622 and 1-516, were constructed by digestion with SmaI or BamH1 respectively. Following restriction enzyme digests, mERβ was religated in pGBT9 and reintroduced into yeast strain Y190. A C-terminal mERP truncation mutant was constructed by excising the BamH1 mERβ fragment in order to get mERβ 516-1458. mERβ, following restriction enzyme digestion, was religated in pGAD10 and reintroduced into yeast strain Y190. To create a mERβ 516-641 mutant, EcoR1 and BamH1 sites were engineered at amino acids 172 and 213, respectively, with PCR primers. The resulting PCR product was ligated into pGBT9 and reintroduced into yeast strain Y190. The correct reading frame was verified by DNA sequencing. An N-terminal EC1 truncation mutant was constructed by excising the EcoR1 EC1 fragment for EC1 1~1900. Again, following restriction enzyme digest, EC1 was self-ligated in PGBT0 and reintroduced into Y190. Expression of mERβ1–516 in pGBT9 was confirmed by a Western blot of the Y190 lysate using the rabbit polyclonal Gal4 DNA binding domain antibody (Upstate Biotechnology, Lake Placid, N.Y.).

Assay of the truncation mutants proved to be a sensitive and specific screen for the identification of the MAD2/ER beta interaction domain. The interaction domain was identified as encompassing amino acids 516 to 622 (FIG. 3A). FIG. 3B summarizes the two hybrid protein interaction results. As is shown in FIG. 3B, the ER beta/MAD2 interaction domain is defined by amino acids 516 to 641 of clone EC1. FIG. 3B also shows that slightly larger regions, containing the interaction domain, support the interaction between ER beta and MAD2, while fragments lacking the 516–622 amino acid domain do not.

GST-Pull Down Assays

GST-fusion protein interaction assays were also performed to examine the interaction between ER beta and MAD2.

EC1 1~1900, the N-terminal mERβ trunction mutant mERβ1–622 (EcoR1/SmaI), and the C-terminal mERβ truncation mutant mERβ516-1458 (BamH1/EcoR1) were ligated into PGEX-4T-1 (Pharmacia Biotech, Piscataway, N.J.). The mERβ 518-622 mutant was constructed by excising the BamH1 mERβ1–622 fragment. Following restriction enzyme digest, mERβ was religated into PGEX-4T-1. Full length ratERβ ligated into PGEX-2TK was obtained from Dr. Myles A. Brown (Dana Farber Cancer Institute, Boston, Mass.). GST-mERβ-622, GST-mERβ516-1458, GST-mERβ516-622 and GST-rERβ were used to express GST fusion proteins as follows.

Fresh overnight cultures of *Eschericia coli* (XL10-Gold: Stratagene; BL21: Novagen) transformed with one of the pGEX4T-1 or pGEX-2TK recombinants were diluted 1:10 in Luria-Bertoni medium (LB) containing ampicillin (100 mg/ml) and incubated at 37° C. with shaking. After 1 hour of growth, isopropyl-β-D-thiogalactopyranoside (IPTG, Calbiochem-Novabiochem, LaJolla, Calif.) was added to a final concentration of 0.1 mM.

For analysis of total bacterial protein content, aliquots of each bacterial culture were pelleted in a microcentrifuge, boiled in SDS sample buffer (10% Glycerol, 50 mM Tris pH 6.8, 1% SDS, 5% β-mercaptoethanol, 0.01% Bromophenol Blue), and loaded onto an SDS-polyacrylamide gel. Proteins were visualized by Coomassie blue staining. The GST fusion proteins were immobilized on Glutathione Sepharose beads.

Recombinant [$^{35}$S]mERβ, [$^{35}$S]hERα and [$^{35}$S]hsMAD2 were produced by using in vitro transcription/translation assay and [$^{35}$S]methionine for labeling (TNT Coupled Reticulocyte Lysate Systems kit, Promega, Madison, Wis., USA). CMV3mERβZEO, CMV3ERα and pET28a(+) hsMAD2 (Dr. R. Benezra, The Memorial Sloan Kettering Cancer Center, New York, N.Y.) were used as templates, respectively.

Recombinant proteins were incubated at 4° in suspension buffer (20 mM Tris pH7.4, 137 mM NaCl, 2 mM EDTA pH7.4, 1% TritonX-100, 10% Glycerol, 25 mM β-glycerolphosphate, 1 mM Na vanadate, 10 mg/ml leupeptin, 10 mg/ml aprotinin, 1 mM PMSF) with either one of the GST fusion proteins immobilized on glutathione-Sepharose beads for 1 hour. Beads were then washed three times in suspension buffer, boiled 5 minutes in SDS sample buffer, and associated proteins resolved by SDS-PAGE. Labeled protein bands in gels were then visualized by autoradiography.

For fusion protein recovery using glutathione-Sepharose (Pharmacia, Piscataway, N.J.), bacterial cultures were pelleted by centrifugation at 5000×g for 5 min at 4° C. and resuspended in 1/10 volume NETN (20 mM Tris pH 8.0, 100 mM NaCl, 1 mM EDTA, 0.5% NP-40). The bacteria were then lysed on ice by mild sonication and centifuged at 10.000×g for 5 min at 4° C. The bacterial supernatant (~10ml) was rocked for 2 hrs at 4° C. with 1 ml of glutathione-Sepharose which had been previously washed three times and resuspended (final concentration 1:1 v/v in NETN). The glutathione-Sepharose beads were then washed three times in NETN. For analysis of bound proteins, the beads were boiled in 1× sample buffer (10% Glycerol, 50 mM Tris pH 6.8, 1% SDS, 5% β-mercaptoethanol, 0.01% BromphenolBlue) and loaded onto SDS-polyacryla­minde gels. Proteins were visualized by Coomassie blue staining.

FIG. 4 shows the GST-fusion protein results. [$^{35}$S] labeled mERβ was incubated with GST-beads (Lane 2) and GST-EC1 beads (Lane 3) followed by SDS-PAGE and autoradiography. Lane 1 shows 10% of the [$^{35}$S]mERβ input (FIG. 4A). In the complementary experiment (FIG. 4B), [$^{35}$S]-labeled hsMAD2 was incubated with GST beads (Lane 2) and GST-mERP beads (Lane 3) followed by SDS-PAGE and autoradiography. Lane 1 shows 15% of [$^{35}$S] MAD2 input (FIG. 4B). GST-fusion protein interaction studies were also done with hERα. [$^{35}$S] labeled hERα was incubated with GST-mERβ (Lane 2, positive control), GST-beads (Lane 3) and GST-EC1 beads followed by SDS-PAGE and autoradiography. Lane 1 shows 5% of the [$^{35}$S] hERα input (FIG. 4C). FIG. 4D shows GST-fusion protein experiments with [$^{35}$S] labeled MAD2 and mERβ mutants. [$^{35}$S]MAD2 was incubated with GST-beads (Lane 2), GST-mERβ 516–622 beads (Lane 3), GST-mERβ 1–622 beads (Lane 4), GST-mERβ 516–1458 beads (Lane 5) and GST-mERβ beads (Lane 6), followed by SDS-PAGE and autoradiography. Lane 1 shows 5% of [$^{35}$S]hsMAD2.

Figure 4A:
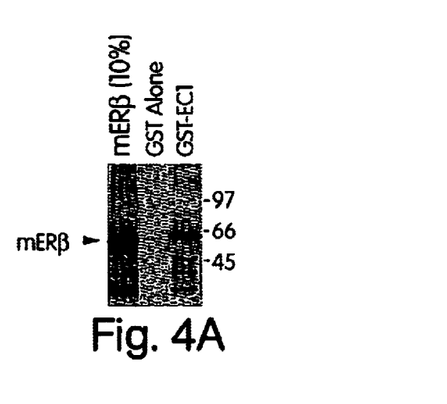
FIG. 4A GST-fusion protein interaction studies with mERβ and EC1.
Figure 4B:
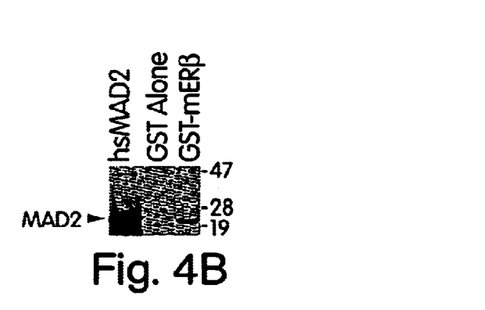
FIG. 4B GST-fusion protein interaction studies with MAD2 and mERβ.
Figure 4C:
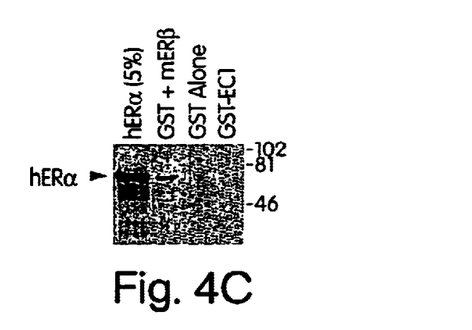
FIG. 4C GST-fusion protein interaction studies with hERα and EC1.
Figure 4D:
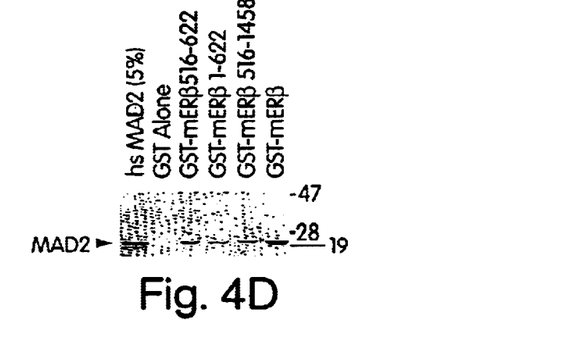
FIG. 4D GST-fusion protein interaction studies with MAD2 and mERβ mutants.

Thus the GST-fusion protein experiments demonstrate that mERβ is brought down, or associates with, the GST-MAD2 clone and, in the converse experiment, MAD2 is brought down by GST-mERβ. Each case demonstrates the protein-protein interaction. In contrast, the results shown in FIG. 4C indicate that while GST-mERβ, as expected, brings down ERα alpha (this is a positive control since it is known that these two proteins heterodimerize), GST alone, or GST MAD2, shown in the third and fourth lanes, respectively, do not bring down ER alpha. This result confirms the two hybrid data, i.e. that ER alpha does not interact with MAD2. FIG. 4D, which shows the results of protein-protein interaction studies between MAD2 and ER beta mutants, also confirms the two hybrid data which identified the MAD2/ER beta interaction domain as including amino acids 516–622. Other experiments indicate that MAD2 does not interact with RAR or RXR (two steroid hormone families members), further underscoring the specificity of the MAD2/ER beta interaction.

PLASMIDS Used for the Above-Described Experiments

Two-Hybrid System mERβ/GalBD+GalAD

Made from pCRII-mERβ (short variant, complete ORF 1–1458) by using EcoR1 as the restriction site.

mERβ1–622/GalBD

Cloned by digesting mERβ/GalBD with Sma1, purification and subsequent religation.

mERβ1–516/GalBD

Cloned by digesting mERβ/GalBD with BamH1, purification and subsequent religation.

mERβ516–641/GalBD

Engineered by PCR (5'primer: EcoR1-site, 3'primer:BamH1-site) with mERβ/GalBD as template and cloned into pGBT9.

mERβ516/1458/GalAD

Cloned by digesting mERβ/GalAD with BAMH1, purification and subsequent religation.

ERα/GalBD+GalAD)

Made from pHEGO (human estrogen receptor alpha) by using EcoR1 as the restriction site.

TIF2/GalAD

Obtained from 2-hybrid screening (human heart library) with mERβ as bait (C9).

TRIP1/GalAD

Obtained from 2-hybrid screening (human brain library) with mERβ as bait (Br5).

GST-Pull Down Assay pGEX-EC1

The N-terminal part of EC1/GalAD (~1.9bp) was excised by EcoR1 and cloned into pGEX-4T-1. XL10-Gold was used for fusion protein expression.

pGEX-ratERβ

From Dr. M. Brown (Dana-Farber Cancer Institute, Boston, Mass.). ratErβ is cloned into pGEX-2TK.

pGEX-mERβ1–622

The N-terminal part of mERβ/GalBD was excised with EcoR1 and Sma1, purified and cloned into pGEX-4T-1. Fusion protein expression was performed in BL21.

pGEX-mERβ516–1458

The C-terminal part of mERβ/GalBD was excised with BamH1 and EcoR1, purified and cloned into pGEX-4T1. Fusion protein expression was performed in BL21.

pGEX-mERβ516–622

The mERβ516–622 mutant was constructed by excising the BamH1 mERβ1–622 fragment. Following restriction enzyme digestion, mERβ was religated into pGEX-4T-1. Fusion protein expression was performed in BL21.

In Vitro Transcription/Translation Assay

[$^{35}$S] hMAD2

DNA template: full-length hs MAD2 ORF was subcloned (EcoR1-in frame with his-tag/Not1) into pET-28A(+) and provided to us by R. Benezra (Science, 1996, 274, 246–248)

[$^{35}$S] mERβ

DNA template: CMV3ERβ-ZEO

[$^{35}$S] hERα

DNA template: CMV3ER

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method for determining whether a test compound is capable of affecting cell division, said method comprising:
    a) contacting said test compound with isolated estrogen receptor beta (ERβ) and mitosis arrest deficient 2 (MAD2), or a binding fragment thereof, under conditions in which ERβ and MAD2, or a fragment thereof, have formed, or are able to form, a complex; and
    b) determining whether said test compound affects said ERβ/MAD2 complex or complex formation, as an indication that said test compound is capable of affecting cell division.

2. The method of claim 1, wherein said MAD2 is encoded by a nucleic acid molecule comprising the sequence set forth in SEQ ID NO: 3.

3. The method of claim 1, wherein said determining is done in vitro.

4. The method of claim 1, wherein said ERβ additionally comprises glutathione-S-transferase (GST) and said complex or complex formation is determined using a GST-fusion protein interaction assay.

* * * * *